United States Patent
Tonn

(10) Patent No.: US 10,175,178 B2
(45) Date of Patent: Jan. 8, 2019

(54) METHOD FOR INSPECTING AN OPHTHALMIC LENS USING OPTICAL COHERENCE TOMOGRAPHY

(71) Applicant: Novartis AG, Basel (CH)

(72) Inventor: Thomas Tonn, Aschaffenburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/653,070

(22) Filed: Jul. 18, 2017

(65) Prior Publication Data

US 2018/0024077 A1 Jan. 25, 2018

Related U.S. Application Data

(60) Provisional application No. 62/364,531, filed on Jul. 20, 2016.

(51) Int. Cl.
*G01B 9/02* (2006.01)
*G01M 11/02* (2006.01)
(Continued)

(52) U.S. Cl.
CPC ....... *G01N 21/958* (2013.01); *G01B 9/02091* (2013.01); *G01M 11/02* (2013.01); *G01N 21/8851* (2013.01); *G01N 2021/9583* (2013.01)

(58) Field of Classification Search
CPC .................................................. G01B 9/02091
See application file for complete search history.

(56) References Cited

U.S. PATENT DOCUMENTS 7,198,777 B2 4/2007 Boppart et al.
8,708,496 B2 4/2014 Gu et al.
(Continued)

FOREIGN PATENT DOCUMENTS

EP 1860421 A2 11/2007
WO 2009058850 A1 5/2009

OTHER PUBLICATIONS

Agrawal et al., "Quantitative Evaluation of Nanoshells as a Contrast Agent for Optical Coherence Tomography", 2005 Optical Society of America, 2005 Conference on Lasers & Electro-Optics, pp. 2049-2051.
(Continued)

*Primary Examiner* — Shawn Decenzo
(74) *Attorney, Agent, or Firm* — Robert A. Ambrose

(57) ABSTRACT

A method for inspecting an ophthalmic lens, such as a contact lens, using Optical Coherence Tomography. The method includes illuminating a sample volume including the lens with a sample light beam which is provided from a light source having a power of at least 2 mW at a wavelength of 1040 nm to 1080 nm and which does not exceed 5 W. In carrying out the method an ophthalmic lens is inspected which has been manufactured such that it comprises scattering centers embedded in and/or on an anterior surface and in and/or on a posterior surface thereof, respectively, and/or distributed throughout a bulk material being delimited by the anterior surface and the posterior surface of the ophthalmic lens. An interference pattern resulting from a superposition of back-scattered light from the sample volume including the ophthalmic lens and a reference light beam provided from the light source may then be analyzed and evaluated.

18 Claims, 3 Drawing Sheets

(51) Int. Cl.
    *G01N 21/88*     (2006.01)
    *G01N 21/958*     (2006.01)

(56)           References Cited

U.S. PATENT DOCUMENTS

| | | | |
|---|---|---|---|
| 9,733,152 B2 * | 8/2017 | Saxer | G01M 11/0207 |
| 2006/0285635 A1 | 12/2006 | Boppart et al. | |
| 2007/0195311 A1 | 8/2007 | Morgan et al. | |
| 2007/0266468 P1 | 12/2007 | Joshi et al. | |
| 2011/0032533 A1 * | 2/2011 | Izatt | G01B 11/2441 |
| | | | 356/497 |
| 2012/0038888 A1 | 2/2012 | Gu et al. | |
| 2015/0168250 A1 | 6/2015 | Saxer et al. | |
| 2016/0313571 A1 * | 10/2016 | Alli | G02C 7/049 |
| 2017/0371180 A1 * | 12/2017 | Harant | G02C 7/049 |
| 2018/0000342 A1 * | 1/2018 | Tang | A61B 3/107 |
| 2018/0120199 A1 * | 5/2018 | Unterkofler | G01M 11/0271 |
| 2018/0173010 A1 * | 6/2018 | Harant | B29D 11/00125 |

OTHER PUBLICATIONS

Boppart, "Advances in Contrast Enhancement for Optical Coherence Tomography", Engineering in Medicine and Biology Society, 2006, 28th IEEE EMBS Annual International Conference, New York City, NY, Aug. 30-Sep. 3, 2006, pp. 121-124.

Xu et al., "Near-infrared dyes as contrast-enhancing agents for spectroscopic optical coherence tomography", 2004 Optical Society of America, Jul. 15, 2004, vol. 29, No. 14, Optics Letters, pp. 1647-1649.

\* cited by examiner

METHOD FOR INSPECTING AN OPHTHALMIC LENS USING OPTICAL COHERENCE TOMOGRAPHY

This application claims the benefit under 35 U.S.C. § 119 (e) of U.S. provisional application Ser. No. 62/364,531 filed on Jul. 20, 2016, incorporated herein by reference in its entirety.

FIELD

The invention relates to a method for inspecting an ophthalmic lens, in particular a contact lens, using optical coherence tomography (OCT).

BACKGROUND

In order to ascertain an appropriate design an accurate manufacturing process is of particular significance for ophthalmic lenses for vision correction, such as, e.g. contact lenses, intra-ocular lenses, corneal onlay lenses and corneal inlay lenses. In order to inspect physical properties of ophthalmic lenses, such as, e.g. a thickness profile, in the past it was necessary to physically cut up the ophthalmic lens along one or more meridians and then obtain an image of the cross-sections of the ophthalmic lens. More recently, a non-destructive testing method has been suggested, namely the application of Optical Coherence Tomography (OCT) for determining physical properties of ophthalmic lenses.

Optical Coherence Tomography (OCT) is an established medical imaging method, in which light of relatively short coherence length is applied to a scattering sample, and with the aid of an interferometer the distances to scattering points of the sample are inspected. The sample is scanned point by point and from the resulting interference patterns a high resolution image of the scanned sample may be deduced. Optical Coherence Tomography is a fast growing imaging technique that has found wide application especially in the biomedical field.

For the inspecting of their physical properties ophthalmic lenses may be scanned using Optical Coherence Tomography such as, e.g. Frequency Domain OCT, Fourier-Domain OCT, complex Fourier OCT, Optical Frequency-domain imaging or swept-source OCT. In the prior art a method for the inspection of ophthalmic lenses using Optical Coherence Tomography has been suggested, which involves adding a scattering agent to the manufactured ophthalmic lens, e.g. by submerging the manufactured ophthalmic lens in a solution including the scattering agent, and then scanning the ophthalmic lens using Optical Coherence Tomography. By submerging the ophthalmic lens in a solution including the scattering agent, usually a pigment, the anterior surface and the posterior surface of the ophthalmic lens, respectively, are altered by the pigments which adhere to or are embedded within the surfaces. As such, these known methods of inspecting ophthalmic lenses using Optical Coherence Tomography are not really non-destructive methods, because the tested sample ophthalmic lens usually must be discarded. Besides being not really non-destructive the known prior art inspection methods of ophthalmic lenses usually suffer the disadvantage of a rather low signal-to-noise ratio, which hinders an easy inspection of physical properties of the ophthalmic lens.

It is therefore an object of the present invention to provide a factual non-destructive method for inspecting an ophthalmic lens using Optical Coherence Tomography (OCT). It is a further object of the invention to improve the signal-to-noise ratio of the OCT image to enable accurate inspection of the physical properties of interest of the ophthalmic lens.

SUMMARY

In the following, whenever features are combined with the term "or", the term "or" is to be understood to also include "and" unless it is evident from the specification that the term "or" must be understood as being exclusive. For example, the term "determining a transition from the fluid to the front surface or the back surface of the ophthalmic lens" is to be understood to include cases in which only the transition to the front surface is determined, furthermore to include cases in which only the transition to the back surface is determined, as well as cases in which both the transition to the front surface and to the back surface is determined.

The present invention suggests a method for inspecting an ophthalmic lens, in particular a contact lens, using Optical Coherence Tomography. The method according to the invention comprises illuminating a sample volume including the ophthalmic lens to be inspected with a sample light beam which is provided from a light source having a power of at least 2 mW at a wavelength of 1040 nm to 1080 nm and which does not exceed 5 W. In carrying out the method according to the invention an ophthalmic lens may be inspected which has been manufactured such that it comprises scattering centers embedded in and/or on an anterior surface, and in and/or on a posterior surface thereof, respectively, and/or distributed throughout a bulk material being delimited by the anterior surface and the posterior surface of the ophthalmic lens. An interference pattern resulting from a superposition of back-scattered light from the defined sample volume including the ophthalmic lens to be inspected and a reference light beam provided from the light source may be analyzed. Thereby raw data corresponding to the ophthalmic lens are segmented from signals corresponding to the surrounding sample volume. Refractive effects of the ophthalmic lens and of the surrounding sample volume are removed from the segmented raw data corresponding to the inspected ophthalmic lens, in order to obtain geometrical data of the inspected ophthalmic lens. The geometrical data may then be transformed into CAD-readable data representing the inspected ophthalmic lens.

In accordance with on aspect of the invention the scattering centers may be formed by one of phase interfaces, boundary surfaces in between components, of which the ophthalmic lens is made, such as, e.g. boundary surfaces in between silicon and a hydrogel, scattering particles, and combinations thereof.

In accordance with another aspect of the invention an ophthalmic lens may be inspected which has been manufactured with scattering centers, which are formed by particles including pigments.

In accordance with yet another aspect of the invention the pigments may be selected to have a particle size of 0.1 µm to 2 µm.

In accordance with another aspect of the invention the sample light beam and the reference light beam may be generated by a superluminescence diode.

In accordance with a still further aspect of the invention, for the inspecting the ophthalmic lens may be arranged within a container allowing unobstructed access of the sample light beam to the ophthalmic lens and unobstructed leaving of back-scattered light from the container, which container preferably is filled with an aqueous liquid, such as water, including deionized water, or a buffered solution, such as a buffered saline solution, or mixtures thereof.

In accordance with yet another aspect of the invention for the inspecting of the ophthalmic lens a probe head comprising an interferometric setup and a scanning mirror and having a water dip window may be used.

In accordance with a still further aspect of the invention, prior to evaluation of the interference pattern signals resulting therefrom may be subjected to a signal enhancement.

In accordance with yet another aspect of the invention the signal enhancement may be accomplished using an optical amplifier, preferably a booster optical amplifier.

In accordance with yet another aspect of the invention for the evaluation of the interference pattern a two-dimensional section image of the ophthalmic lens may be computed and optionally displayed.

In accordance with a further aspect of the invention from the evaluation of the interference pattern a three-dimensional image of the ophthalmic lens may be computed and optionally displayed.

In accordance with yet a further aspect of the invention raw data resulting from an evaluation of the interference pattern may be subjected to an inverse raytracing.

In accordance with another aspect of the invention a mechanical model of the ophthalmic lens may be determined which is represented by CAD data.

In accordance with yet another aspect of the invention evaluating the interference pattern may include determining a feature of the ophthalmic lens selected from the group consisting of a thickness profile of the ophthalmic lens, a shape of the anterior surface and/or the posterior surface of the ophthalmic lens, a curvature of the ophthalmic lens, a power of the ophthalmic lens, an edge profile of the ophthalmic lens, and combinations thereof.

In accordance with still another aspect of the invention evaluating the interference pattern may include providing at least one image of the anterior surface and/or the posterior surface of the ophthalmic lens, respectively, and inspecting the at least one image for defects.

In accordance with a still further aspect of the invention the ophthalmic lens may be a contact lens.

In accordance with another aspect of the invention the contact lens may be a toric contact lens.

In accordance with a further aspect of the invention the contact lens may be a silicone hydrogel lens.

In accordance with yet another aspect of the invention the contact lens may be a hydrated contact lens.

In order to improve the signal-to-noise ratio in the method for inspecting an ophthalmic lens, in particular a contact lens, using optical coherence tomography in accordance with the invention the sample light beam may be provided from a light source having a power of at least 2 mW at a wavelength of 1040 nm to 1080 nm. In order for the interferometer setup to be operable without any further safety precautions, the power of the light source must not exceed 5 W. The ophthalmic lens to be inspected may be manufactured such that it comprises scattering centers. The scattering centers may be embedded in and/or on an anterior surface and in and/or on a posterior surface thereof, respectively, and/or distributed throughout a bulk material, which is delimited by the anterior surface and the posterior surface of the ophthalmic lens. An interference pattern resulting from a superposition of back-scattered light from the defined sample volume including the ophthalmic lens to be inspected and a reference light beam provided from the light source may be analyzed. Thereby raw data corresponding to the ophthalmic lens are segmented from signals corresponding to the surrounding sample volume. Refractive effects of the ophthalmic lens and of the surrounding sample volume are removed from the segmented raw data corresponding to the inspected ophthalmic lens, in order to obtain geometrical data of the inspected ophthalmic lens. The geometrical data may then be transformed into CAD-readable data representing the inspected ophthalmic lens.

The scattering centers may be one of phase interfaces, boundary surfaces in between components, of which the ophthalmic lens is made, such as, e.g. boundary surfaces in between silicon and a hydrogel, scattering particles, and combinations thereof.

The scattering centers may be or may include scattering particles, which may be formed within and/or on the ophthalmic lens only during the manufacture process thereof. It may prove advantageous, if the scattering particles are pigments, such as e.g. may be used to manufacture ophthalmic lenses having a desired color. Such pigments include, but are not limited to Green CR203, Yellow Iron Oxide, and combinations thereof. The pigments can be or may include a water-insoluble salt that forms in situ on the surfaces of the ophthalmic lens and/or throughout the bulk material. The water-insoluble salt may, e.g. be or include a silver salt.

The pigments may be selected to have a particle size of 0.1 µm to 2 µm. In this context the particle size is defined as an equivalent diameter of the particles, the equivalent diameter being the diameter of an equivalent sphere having about the same volume as an arbitrarily shaped particle.

The sample light beam and the reference light beam may be provided e.g. from a laser light source having the required wavelength and short coherence length. For reasons of reduced complexity of the light source and the interferometer setup, the sample light beam and the reference light beam may be generated by a superluminescence diode.

For the inspecting process the ophthalmic lens may be placed within a container, allowing an unobstructed incidence of the sample light beam to the ophthalmic lens and an unobstructed emergence of back-scattered light from the container. In an exemplary embodiment for the above-mentioned purpose the container may e.g. be provided with a window. The container preferably may be filled with an aqueous liquid, such as water, including deionized water, or a buffered solution, such as a buffered saline solution, or mixtures thereof. The wavelength of the light source may be optimized with respect to the aqueous solution, which has a minimum of absorption in the wavelength range from 1040 nm to 1080 nm. It should be noted though, that the inspection of the ophthalmic lens using Optical Coherence Tomography may also be performed in air. Having the ophthalmic lens immersed in aqueous liquid, however, is preferred, because the sensitivity of the inspection may be increased.

The inspecting of the ophthalmic lens immersed in aqueous liquid may be performed using a probe head which comprises an interferometric setup and a scanning mirror and which has a water dip window. The use of a water dip window may facilitate the placement of the ophthalmic lens within the container. The water dip window may be tilted slightly in order to avoid a back reflection of the sample light beam at the window. The interferometric setup may be a low coherence interferometer of the type of a Michelson interferometer. With the aid of the scanning mirror the sample light beam may be scanned across the respective anterior surface of posterior surface of the ophthalmic lens.

The signal-to-noise ratio may be increased even further by subjecting the signals resulting from the superposition of the back-scattered light and the reference light beam prior to evaluation, to a signal enhancement. Thus, the sensitivity of the inspection improved.

The signal enhancement may be accomplished using e.g. an optical amplifier, preferably a booster optical amplifier. The booster optical amplifier amplifies an optical signal directly, without the need to first convert it to an electrical signal.

From the evaluation of the interference pattern a two-dimensional section image of the ophthalmic lens may be computed. Thus, a sectioned image may be obtained without having to actually severe the ophthalmic lens. Optionally the computed image may be displayed. In order to compensate optical distortions, which result from the optical power of the ophthalmic lens the interference pattern may be subjected to an inverse raytracing. Thus, a corrected mechanical model may be obtained from which dimensions of the ophthalmic lens may be determined.

Not only is it possible to compute sectioned images of the ophthalmic lens, but from the evaluation of the interference pattern also a three-dimensional image of the ophthalmic lens may be computed. Optionally the computed image may be displayed. For the achievement of a corrected mechanical model of the ophthalmic lens the raw data resulting from the evaluation of the interference pattern may be subjected to an inverse raytracing.

By the application of a smoothing method such as, e.g. inverse raytracing, which may also be designated as Dewarping, a mechanical model of the ophthalmic lens may be determined which may be represented by CAD data. By an application of OCT in a first step a 3-D image of the ophthalmic lens may be obtained. The 3-D image corresponds to points of increased intensity within a scanned volume. By a process called segmentation the 3-D image of the ophthalmic lens may be separated from the scanned volume. In this process step also stray light resulting e.g. from particles floating in the scanned volume may be eliminated. In order to compensate optical distortions which result from the optical power of the ophthalmic lens the image data are subjected to a smoothing process, such as, e.g. inverse raytracing. The result is a corrected mechanical model of the ophthalmic lens, which may be represented by CAD data. The corrected mechanical model may be used to determine the desired mechanical and optical properties of the ophthalmic lens. If the mechanical model of the inspected ophthalmic lens is represented by CAD data it may be directly compared with original target data which may be stored in form of original CAD data.

The interference pattern which results from the superposition of the light which is back-scattered by the ophthalmic lens and the reference light beam may be evaluated to determine various physical properties of the ophthalmic lens. These evaluations include but are not limited to determining a thickness profile of the ophthalmic lens, determining a shape of the anterior surface and/or the posterior surface of the ophthalmic lens, determining a curvature of the ophthalmic lens, determining a power of the ophthalmic lens, controlling an edge profile of the ophthalmic lens, and combinations thereof.

The evaluation of the interference pattern may also include providing at least one image of the anterior surface and/or the posterior surface of the ophthalmic lens, respectively, and inspecting the at least one image of the respective surface for defects. In the determination of an image of a respective anterior surface or posterior surface of the ophthalmic lens special methods such as, e.g. inverse ray tracing, may be employed, in order to produce a more photorealistic image from the optically gathered data, including a corrected mechanical lens model. From the corrected mechanical lens model then dimensions of the ophthalmic lens may be obtained.

The method according to the invention may be employed to inspect physical properties of ophthalmic lenses and to control the quality of the manufacturing process thereof. The method may be employed in particular for the inspection and manufacture control of contact lenses. The contact lens can be a spheric or aspheric contact lens and may even be a toric contact lens. The contact lens may be manufactured from the common contact lens materials, including silicone hydrogels. The method may be performed on hydrated or on unhydrated contact lenses. In order to obtain physical properties which reflect the properties of the contact lens in use, inspections of the hydrated contact lens are preferred.

BRIEF DESCRIPTION OF THE DRAWINGS

Further details and advantages of the invention will become apparent from the following description with reference to the schematic drawings, in which.

DETAILED DESCRIPTION OF EMBODIMENTS

Figure 1:
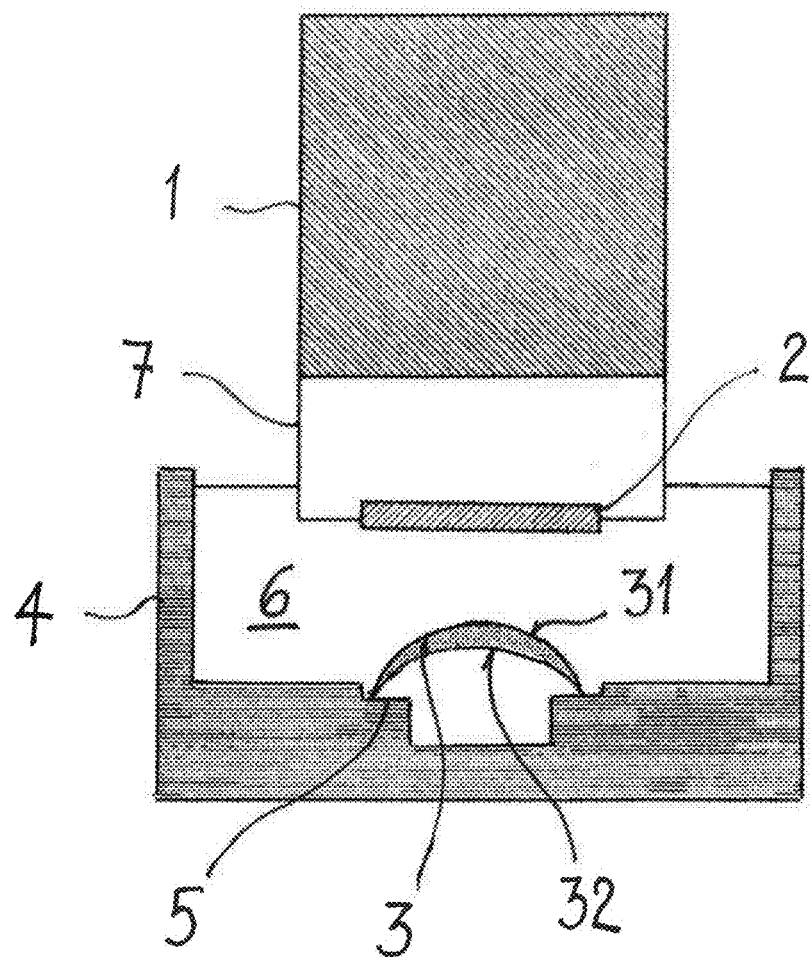
FIG. 1 shows a schematic representation of an inspection setup for carrying out the method according to the invention.

The inspection setup which is shown schematically in FIG. 1 comprises a probe head 1, which encloses an interferometric setup (not shown) and a scanning mirror (not shown). The interferometric setup is a low-coherence interferometer of the type of a Michelson interferometer, where distance information concerning a scanned sample is extracted from time delays of reflected signals. Such a low-coherence interferometer is the basis of Optical Coherence Tomography (OCT), which is well known in the art, and capable to provide images of a sample with micrometer resolution. A sample light beam, which is produced by a beam splitter of the low-coherence interferometer, is directed via a water dip window 2 towards an ophthalmic lens 3, in particular a contact lens, which is held on a lens support 5 within the container 4. The container 4 has an open top, thus allowing unobstructed access of the sample light beam to the ophthalmic lens 3 and unobstructed leaving of back-scattered light from the container 4 to the water dip window 2 again. The container 4 is filled with an aqueous liquid 6, such as water, including deionized water, or a buffered solution, such as a buffered saline solution, or mixtures thereof. A front portion 7 of the probe head 1 protrudes into the aqueous liquid 6 such, that the water dip window 2 is immersed in the aqueous liquid 6. The water dip window 2 is slightly tilted with respect to a vertical direction, so that back reflections at the water dip window 2 do not reach the low-coherence interferometer setup within the probe head 1. It should be noted that in an alternative embodiment the interferometric setup and the scanning mirror may be arranged spaced from the container accommodating the contact lens. In that case the sample light beam may be guided to the container via a light wave guide.

In the low-coherence interferometer setup the sample light beam and a reference light beam are generated by guiding incident light from a light source through a beam splitter. The light source may be a superluminescence diode having a power of at least 2 mW at a wavelength of 1040 nm to 1080 nm. The wavelength of 1040 nm to 1080 nm corresponds to a local minimum of absorption of the aqueous liquid 6. A maximum power of the superluminescence diode does not exceed 5 W. The sample light beam is directed onto the ophthalmic lens 3, which is secured on the lens support 5 within the container. Scattering particles, which are embedded on or in a front surface 31 and a back surface 32 and or within bulk material of the contact lens 3, which is delimited by the front surface 31 and the back surface 32 reflect the incident sample light beam. The back scattered light enters the probe head 1 through the water dip window 2 and is superposed with the reference light beam. The resulting interference pattern is evaluated to determine the physical properties of interest.

Contrary to the inspecting methods of the state of the art the scattering particles are not added to the contact lens 3 only prior to the inspection. In accordance with the invention a contact lens 3 is inspected which already includes scattering centers on its surfaces and/or within its bulk material. Thus, the scattering centers form an integral part of the contact lens 3. The scattering centers may be formed by one of phase interfaces, boundary surfaces in between components, of which the ophthalmic lens is made, such as, e.g. boundary surfaces in between silicon and a hydrogel, scattering particles, and combinations thereof. In a preferred embodiment the scattering centers may be formed by scattering particles. The scattering particles may be a constituent of the prepolymer or monomeric raw material, from which the contact lens is manufactured. Alternatively, the scattering particles may be added to the contact lens during the manufacture process.

The scattering particles may be or may include pigments. The pigments may be selected to have a particle size of 0.1 µm to 2 µm. In this context the particle size is defined as an equivalent diameter of the particles, the equivalent diameter being the diameter of an equivalent sphere having about the same volume as an irregularly shaped particle. Instead of adding the pigments already to the raw material they may be formed in situ from a pigment precursor while the contact lens 3 is being manufactured.

In order to increase the signal-to-noise ratio and to improve the sensitivity of the inspection the signals resulting from the superposition of the back-scattered light and the reference light beam may be subjected to a signal enhancement prior to evaluation. The signal enhancement may be accomplished using e.g. an optical amplifier, preferably a booster optical amplifier, which is arranged within the probe head 1. The booster optical amplifier is capable of amplifying an optical signal directly, without the need to first convert it to an electrical signal.

Figure 2:
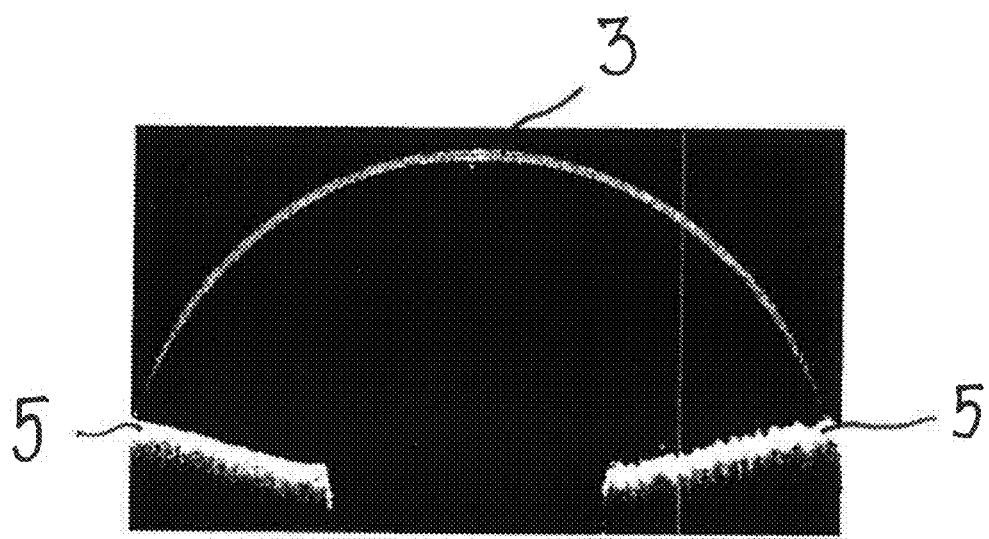
FIG. 2 shows a two-dimensional section image of a contact lens.

FIG. 2 shows a two dimensional image of the contact lens 3, which has been computed from the evaluation of the interference pattern resulting from a superposition of back-scattered light from the lens and the reference light beam. The image shows a sectioned view of the contact lens 3, without having to section the lens physically. For the inspection the contact lens 3 has been immersed in an aqueous liquid 6 and rests on a lens support 5. The image is computed from raw data which are obtained from the evaluation of the interference pattern. In order to compensate optical distortions which result from the optical power of the contact lens 3 and further in order to obtain corrected mechanical dimensions of the contact lens 3 the raw data may be subjected to a smoothing algorithm, such as e.g. inverse raytracing. Because the raw data representing the mechanical dimensions of the contact lens do not change abruptly, with a smoothing algorithm the resolution of the image may be enhanced by up to a factor of about 10. It should be noted that the term resolution is not solely limited to an optical resolution but it is also expresses an accuracy of mechanical dimensions of the inspected contact lens.

Figure 3:
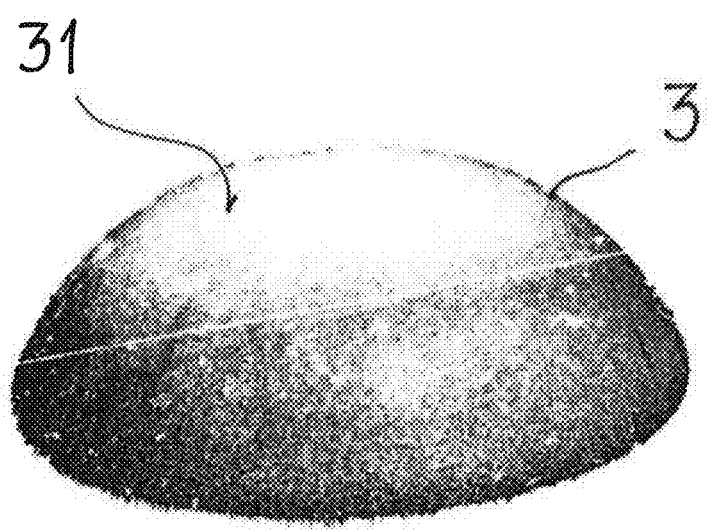
FIG. 3 shows a three-dimensional image of a contact lens.

FIG. 3 shows a three-dimensional image of the contact lens 3, with a view at the anterior surface 31 thereof. The image is computed from raw data resulting from the superposition of back-scattered light from the contact lens 3 and the reference light beam. The inspection time for a scan of the whole contact lens 3, which is immersed in aqueous liquid, is about 10 sec.

Figure 4:
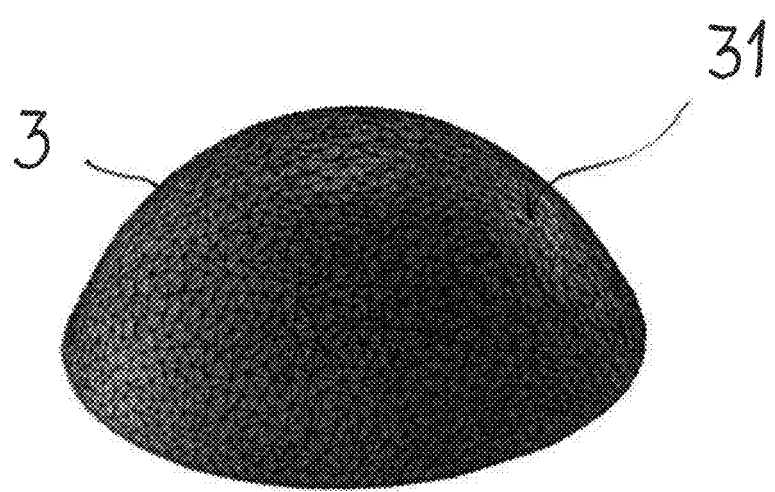
FIG. 4 shows a three-dimensional image of a contact lens after a smoothing process.

FIG. 4 shows another three-dimensional image of the contact lens 3, which a view at the anterior surface thereof. In order to compensate optical distortions which result from the optical power of the contact lens 3 and further in order to obtain corrected mechanical dimensions of the contact lens 3 the raw data have been subjected to a smoothing algorithm, such as e.g. inverse raytracing. Because the raw data representing the mechanical dimensions of the contact lens do not change abruptly, with a smoothing algorithm the resolution of the image may be enhanced by up to a factor of about 10. It should be noted that the term resolution is not solely limited to an optical resolution but it is also expresses an accuracy of mechanical dimensions of the inspected contact lens.

The interference pattern which results from the superposition of the light which is back-scattered by the contact lens and the reference light beam may be evaluated to determine various physical properties of the contact lens 3. These evaluations include but are not limited to determining a thickness profile of the contact lens 3, determining a shape of the anterior surface 31 and/or the posterior surface 32 of the contact lens 3, determining a curvature of the contact lens 3, determining a power of the contact lens 3, controlling an edge profile of the contact lens 3, and combinations thereof.

The evaluating of the interference pattern may also include providing at least one image of the anterior surface 31 and/or the posterior surface 32 of the contact lens 3, respectively, and inspecting the at least one image of the respective surface for defects. In order to compensate optical distortions which result from the optical power of the contact lens 3 and further in order to obtain corrected mechanical dimensions of the contact lens 3 the raw data may be subjected to a smoothing algorithm, such as e.g. inverse raytracing. Because the raw data representing the mechanical dimensions of the contact lens do not change abruptly, with a smoothing algorithm the resolution of the image may be enhanced by up to a factor of about 10. Again it should be noted that the term resolution is not solely limited to an optical resolution but it is also expresses an accuracy of mechanical dimensions of the inspected contact lens.

The method according to the invention generally may be employed to inspect physical properties of ophthalmic lenses and to control the quality of the manufacturing process thereof. The method may be employed in particular for the inspection and manufacture control of contact lenses. The contact lens can be a spheric or aspheric contact lens and may even be a toric contact lens. The contact lens may be manufactured from the common contact lens materials, including silicone hydrogels. The method may be performed on hydrated or on unhydrated contact lenses. In order to obtain physical properties which reflect the properties of the contact lens in use, inspections of the hydrated contact lens are preferred.

Although the invention has been described with reference to a specific setup for the inspection of a contact lens immersed in an aqueous liquid and including a low-coherence interferometer setup, it is evident to the person skilled in the art that this embodiment has been described only by way of example, and that various changes and modifications are conceivable without departing from the teaching underlying the invention. While the invention has been described with particular focus on the determination of various physical properties and parameters of contact lenses, it must be noted that the testing method may as well be carried out with ophthalmic lenses in general in order to determine characteristic properties of ophthalmic lenses or optimum parameters e.g. of a plasma treatment of the ophthalmic lenses. Therefore, the invention is not intended to be limited by the embodiment described but rather is defined by the appended claims and their equivalents.

The invention claimed is:

1. Method for inspecting an ophthalmic lens using Optical Coherence Tomography comprising
   illuminating a defined sample volume including the ophthalmic lens to be inspected with a sample light beam which is provided from a light source having a power of at least 2 mW at a wavelength of 1040 nm to 1080 nm and which does not exceed 5 W, the ophthalmic lens having been manufactured such that it comprises scattering centers embedded in and/or on an anterior surface and in and/or on a posterior surface thereof, respectively, and/or distributed throughout a bulk material being delimited by the anterior surface and the posterior surface of the ophthalmic lens,
   detecting signals corresponding to an interference pattern resulting from a superposition of back-scattered light from the defined sample volume including the ophthalmic lens to be inspected and a reference light beam provided from the light source,
   analyzing the detected signals and segmenting raw data corresponding to the ophthalmic lens from signals corresponding to the surrounding sample volume,
   removing refractive effects of the ophthalmic lens and of the surrounding sample volume from the segmented raw data corresponding to the inspected ophthalmic lens in order to obtain geometrical data of the inspected ophthalmic lens, and
   transforming the geometrical data into CAD-readable data representing the inspected ophthalmic lens.

2. The method according to claim 1, wherein the scattering centers are formed by one of phase interfaces, boundary surfaces in between components of which the ophthalmic lens is made, scattering particles, and combinations thereof.

3. The method according to claim 1, wherein the scattering centers are formed by particles including pigments.

4. The method according to claim 3, wherein the pigments have been selected to have a particle size of 0.1 μm to 2 μm.

5. The method according to claim 1, wherein the sample light beam and the reference light beam are generated by a superluminescence diode.

6. The method according to claim 1, wherein for the inspecting the ophthalmic lens is held within a container allowing unobstructed access of the sample light beam to the ophthalmic lens and unobstructed leaving of back-scattered light from the container, which container is filled with an aqueous liquid selected from the group consisting of water, deionized water, an aqueous buffered solution, a buffered saline solution, or mixtures thereof.

7. The method according to claim 6, wherein for the inspecting of the ophthalmic lens a probe head comprising an interferometric setup and a scanning mirror and having a water dip window is used.

8. The method according to claim 1, wherein prior to evaluation of the interference pattern signals resulting therefrom are subjected to a signal enhancement.

9. The method according to claim 8, wherein the signal enhancement is accomplished using an optical amplifier.

10. The method according to claim 1, wherein from the evaluation of the interference pattern a two-dimensional section model of the ophthalmic lens is computed.

11. The method according to claim 1, wherein from the evaluation of the interference pattern a three-dimensional model of the ophthalmic lens is computed.

12. The method according to claim 1, wherein the geometrical data representing the inspected ophthalmic lens are subjected to an inverse raytracing.

13. The method according to claim 1, wherein the geometrical data representing the inspected ophthalmic lens are evaluated to determine a feature of the ophthalmic lens selected from the group consisting of a thickness profile of the ophthalmic lens, a shape of the anterior surface and/or the posterior surface of the ophthalmic lens, a curvature of the ophthalmic lens, a power of the ophthalmic lens, an edge profile of the ophthalmic lens, and combinations thereof.

14. The method according to claim 1, wherein the CAD-readable data representing the inspected ophthalmic lens are used to provide an image of at least the anterior surface and/or the posterior surface of the ophthalmic lens, respectively, and for inspecting the respective image for defects.

15. The method according to claim 1, wherein the ophthalmic lens is a contact lens.

16. The method according to claim 15, wherein the contact lens is a toric contact lens.

17. The method according to claim 15, wherein the contact lens is a silicone hydrogel lens.

18. The method according to claim 15, wherein the contact lens is a hydrated contact lens.

* * * * *